United States Patent [19]

Wagner

[11] Patent Number: 5,147,369
[45] Date of Patent: Sep. 15, 1992

[54] FORCEPS AND METHOD FOR NUCLEAR FRAGMENT REMOVAL

[76] Inventor: Michael A. Wagner, 5127 Vista Hermosa, Long Beach, Calif. 90815

[21] Appl. No.: 723,797

[22] Filed: Jul. 1, 1991

[51] Int. Cl.$^5$ .............................................. A61F 9/00
[52] U.S. Cl. .................................. 606/107; 606/205; 606/210
[58] Field of Search .................. 606/107, 205–211; 294/99.2; 30/113.2, 229; 128/751, 898; 604/22

[56] References Cited

U.S. PATENT DOCUMENTS

| | | | |
|---|---|---|---|
| 896,338 | 8/1908 | Tolman | 294/99.2 |
| 1,461,670 | 7/1923 | Mills | 294/99.2 |
| 2,994,321 | 8/1961 | Tischler | 128/751 |
| 3,895,636 | 7/1975 | Schmidt | 606/205 |
| 3,964,468 | 6/1976 | Schulz | 128/751 |
| 4,213,460 | 7/1980 | Weiner | 606/211 |
| 4,226,459 | 10/1980 | Natalicio | 294/99.2 |
| 4,888,015 | 12/1989 | Domino | 606/207 |

FOREIGN PATENT DOCUMENTS 41289 12/1929 Denmark ........................... 294/99.2

Primary Examiner—C. Fred Rosenbaum
Assistant Examiner—William Lewis
Attorney, Agent, or Firm—Charles H. Thomas

[57] ABSTRACT

Forceps are provided for use in removing nuclear fragments of the lens of an eye during eye surgery. It is not unusual during phaco emulsification surgery on the lens of an eye for the capsule of the lens to become torn and for vitreous humor to enter the lens capsule through the tear and engulf the nuclear fragments remaining in the lens to migrate through a tear in the lens capsule into the vitreous humor. The forceps of the invention allow such nuclear fragments to be removed far more easily and with less likelihood of complications than has heretofore been possible. The forceps are formed of a pair of elongated arms at the tips of which tiny hemispherical or oval cup-shaped implements are mounted. These implements are concave at their mutually facing central regions. The perimeters of the implements from cutting edges that are capable of being brought into mutual contact throughout to entrap loose nuclear fragments therebetween.

15 Claims, 1 Drawing Sheet

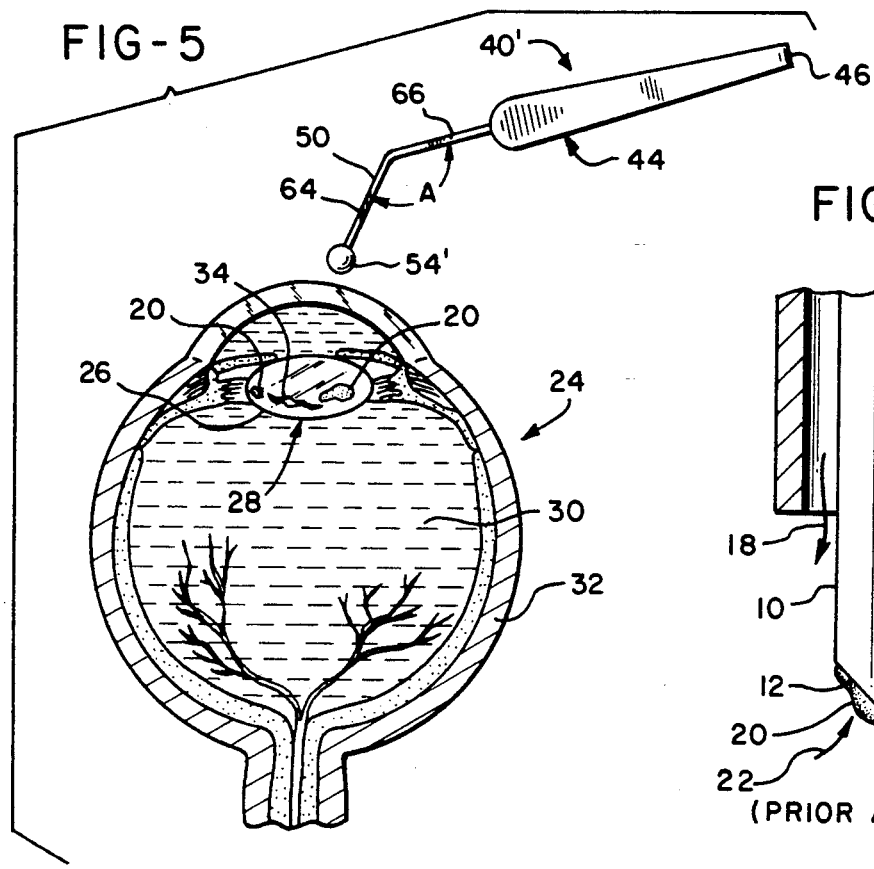
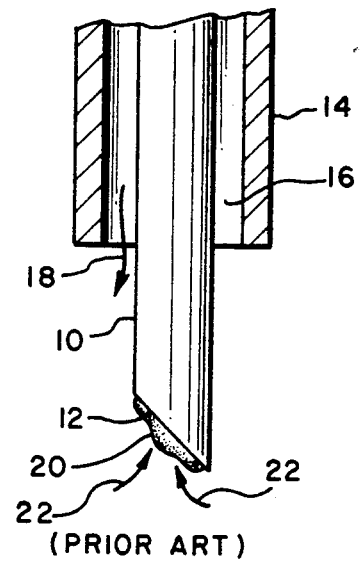
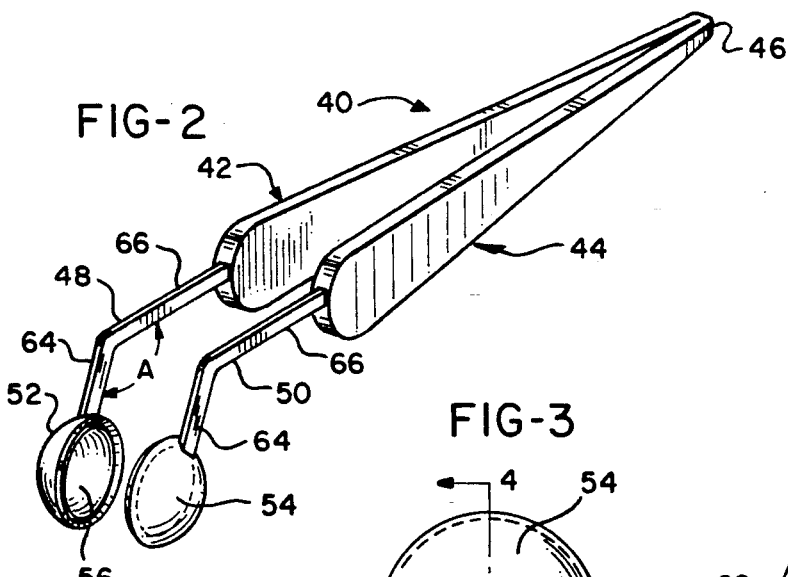
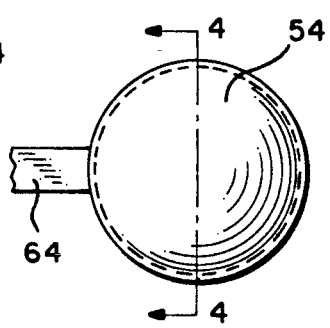
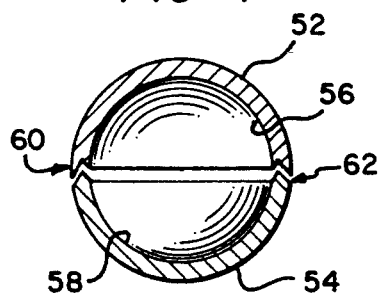

FORCEPS AND METHOD FOR NUCLEAR FRAGMENT REMOVAL

BACKGROUND OF THE INVENTION

1. Field of the Invention

The present invention relates to a method and forceps for removing nuclear fragments of a lens during eye surgery.

2. Description of the Prior Art

In some people, especially the elderly, the condition of one or both eyes will deteriorate and the patient may develop cataracts in either or both eyes. The development of cataracts is a condition in which the lens of the eye becomes at least partially cloudy or even opaque. When this condition develops it is necessary to remove the internal portions of the natural lens of the eye in order to restore the patient's sight. The natural lens is usually replaced with a tiny artificial prosthetic plastic lens.

The exterior surface of the lens of the eye is termed the capsule. The capsule completely surrounds and encloses an inner lining of soft material termed the cortex. The cortex in turn encapsulated the nucleus of the lens therewithin. The nucleus of the lens is a relatively hard substance, as contrasted with the surrounding cortex. It is usually within the nucleus that cataracts develop and removal of the nucleus is essential to restoration of the patient's sight.

There are several methods of removal of the internal portions of the lens of an eye in performing cataract surgery. One method is to "express" the lens. In this method a relatively large incision is made in the capsule of the lens and the nucleus of the lens is forced out of the capsule by external pressure. The disadvantage of this technique is that the recuperation time is lengthy, typically about a month. During this period, the patient cannot exert any strain or lift objects of even moderate weight or complications are likely to develop.

Another technique for removal of the internal parts of the lens in cataract surgery is phaco emulsification. In this technique only a local anesthetic is used on the patient and phaco emulsification needle is inserted into the lens of the eye through a very small incision. The phaco emulsification needle is vibrated at ultrasonic frequency to break up the nucleus of the lens using ultrasound. The needle is hollow and suction is exerted through a central axial passageway of the needle, while fluid to carry the emulsified nuclear particles is injected into the capsule of the lens through an annular passageway that surrounds the hollow needle. By breaking up the lens nucleus ultrasonically and aspirating the nuclear particles in a flushing fluid the nucleus of the lens can be evacuated from the capsule. Preferably also the cortex of the lens is similarly evacuated from the capsule using an irrigation-aspiration tip. Because the incision is so tiny a patient can resume normal activities the following day after the successful performance of lens nucleus removal by phaco emulsification.

One recurring problem which has existed with phaco emulsification lens removal is that with the use of a rapidly vibrating, tiny sharp needle it is not uncommon for accidental incisions to be made in the wall of the capsule facing the vitreous humor of the eyeball. When this occurs vitreous humor from within the eyeball will well up into the capsule through the slit or tear in the capsule. Such accidental slits or incisions in the capsule wall are of no great consequence in themselves. However, not infrequently ultrasonically disintergrated fragments of the nucleus will migrate from the capsule through an incision or slit created during phaco emulsification and pass into the vitreous humor in the eyeball.

The presence of such nuclear fragments in the vitreous humor can create severe complications. Specifically, unlike particles of the cortex, nuclear fragments of the lens will not dissolve by themselves in the vitreous humor. To the contrary, they remain and cause inflammation and increased pressure within the eyeball. Therefore, it is very important for any nuclear fragments to be removed at once before they pass from the lens capsule deep into the vitreous humor. Once nuclear fragments descend into the vitreous humor in the enclosure of the sclera they become very difficult for the surgeon to locate. When this occurs the surgeon has no choice but to close up the eye. Subsequent, more complex surgery must then be performed at a later time by a vitriol-retinal surgeon, during which the patient must be given a general anesthetic.

The phaco emulsification needle should not be used for the continued removal of nuclear fragments of the lens from the lens capsule once vitreous humor has entered the capsule through a slit in the capsule wall. That is, the surgeon should not attempt to aspirate the nuclear fragments from the vitreous humor that has entered the capsule by bringing the aspirating tip of the needle to bear upon any such nuclear fragments in the vitreous humor. The vitreous humor is a soft, jelly-like sustance which tends to be somewhat cohesive. When suction is exerted through the phaco emulsification needle, force is transmitted through the substance of the vitreous humor to the interior walls of the sclera. Such forces which are transmitted through the vitreous humor can even cause detachment of the retina, which is a very serious complication to the surgery.

According to conventional acceptable techniques phaco emulsification must cease once a slit has been created in the side of the capsule facing the vitreous humor. The surgeon then attempts to remove any remaining nuclear fragments using a lens loop. A lens loop is an implement in which a tiny loop is formed in the end of a wire. The loop is inserted into the lens capsule and positioned beneath a nuclear fragment remaining in the capsule. The surgeon then attempts to drag the fragment free from the vitreous humor that has entered the capsule. Each fragment must be removed one by one. However, since the vitreous humor is so sticky, the nuclear fragments are very difficult to extract from the vitreous humor using a lens loop.

SUMMARY OF THE INVENTION

The present invention involves a method and apparatus for removing nuclear fragments of a lens during eye surgery following penetration of the lens capsule wall facing the vitreous humor which does not entail the hazards of such removal using a phaco emulsification needle nor the difficulties encountered using a lens loop. According to the method of the invention special purpose forceps are provided for use in removing nuclear fragments of the lens of an eye. The forceps are comprised of a pair of elongated arms both having mutually attached ends and opposite free ends. The free ends of the arms extended in diverging fashion from each other and are biased apart. The free ends of the arms terminate in mutually facing cup-shaped implements which are concave at their mutually facing central regions.

These implements have perimeters which encircle the central regions and which form cutting edges that are capable of being brought into mutual contact throughout.

Each of the implements on the tips of the arms of the forceps preferably has either the hollow configuration of one half of a spheroid or a hollow, hemispherical configuration. That is, when the implements are pressed together and meet about their perimeters they preferably form either a sphere or an oval body. The minimum dimension of each implement from one side of the perimeter to the other is preferably between three and about six millimeters. Forceps having implement sizes of two, three, four, five and six millimeters as the smallest dimension, or smallest diameter, may be provided to suit particular surgeons or for use with nuclear fragments of different sizes.

It is important that the perimeters of the implements meet and form sharp cutting edges throughout their entire circumferences. Either or both of the perimeters of the implements of the forceps may be formed with a blade edge. In the one embodiment of the invention one of the cutting edges is formed with a blade edge and the other of the cutting edges is formed with an indentation adapted to receive the blade edge. In this way a nuclear fragment can be entrapped within the confines of the cup-shaped implements, and the contents of the enclosure encapsulated within the cup-shaped implements can be cleanly cut and excised from the surrounding vitreous humor. In this way pulling and tension on the surrounding vitreous humor is avoided, and the captured nuclear fragments can be removed from the vitreous humor with less danger of retinal detactment.

To facilitate insertion of the tips of the forceps into the eye of a patient, while minimizing the extent to which the forceps obscure the view of the surgeon, the free ends of the arms of the forceps preferably include linear extremities adjacent the tips which form an obtuse angle with adjacent linear portions of the arms by means of which the surgeon grasps the forceps to manipulate them. This obtuse angle is preferably between about 135 and 150 degrees.

In another aspect the invention may be considered to be a method of removing nuclear fragments of a lens during eye surgery utilizing forceps which are equipped with a pair of mutually facing cup-shaped implements that have recessed central regions and mating peripheral cutting edges surrounding the recessed central regions. According to the method of the invention a nuclear fragment of a lens which has become dislodged in an eye of a patient is visually located by the surgeon. The cup-shaped implements of the forceps are moved into the eye to positions on opposite sides of the nuclear fragment. The implements are pressed together to encapsulate the nuclear fragment therebetween and to isolate it from the interior of the eye. The implements are held together while withdrawing them from the eye, thereby withdrawing the nuclear fragment therefrom as well.

By utilizing the forceps and the method of the invention an eye surgeon is able to successfully extract nuclear fragments from the eye of a patient with a considerably reduced danger of creating retinal detachment or other complications during eye surgery when there is a cut or tear in the wall of the capsule. The forceps of the invention can eliminate the need for a second operation during which the patient would have to be placed under a general anesthetic.

The invention may be described with greater clarity and particularity by reference to the accompanying drawings.

DESCRIPTION OF THE DRAWINGS

FIG. 1 is an enlarged sectional detail of the tip of a conventional phaco emulsification needle.

FIG. 2 is a perspective view of one embodiment of forceps according to the invention.

FIG. 3 is a side elevational detail viewed from the side one of the implements of the forceps of FIG. 2.

FIG. 4 is a sectional elevational detail taken along the lines 4—4 of FIG. 3.

FIG. 5 is a diagrammatic view showing use of an alternative embodiment of forceps according to the invention for the removal of nuclear fragments from an eye.

DESCRIPTION OF THE EMBODIMENTS AND IMPLEMENTATION OF THE METHOD

FIG. 1 is a greatly enlarged view illustrating the tip of a phaco emulsification instrument of the type utilized for removal of the internal parts of a lens from a patient in the performance of cataract surgery. The phaco emulsification instrument has a narrow, stainless steel hollow needle 10 having a cutting surface 12 at its extremity. The needle 10 is subjected to ultrasonic vibration during the performance of cataract surgery. A collapsible, silicone tube 14 is disposed coaxilly about the needle 10 and an aqueous flushing solution is injected into the capsule of the lens of the eye of the patient through the annular passageway 16, as indicated by the directional arrow 18. Suction is exerted internally within the passage defined within the needle 10, so that nuclear fragments, such as the nuclear fragment indicated at 20, can be drawn up into the passageway defined within the needle 10 and removed from the lens capsule. The aspirating forces are indicated by the directional arrows at 22.

In the performance of the removal of the nucleus of a lens from the eye of a patient, indicated generally at 24 in FIG. 5, the phaco emulsification needle 10 is inserted into the capsule 26 of the lens 28, and the relatively hard nucleus of the lens isa ultrasonically broken up into fragments indicated at 20. As illustrated in FIG. 5, one of the surfaces of the capsule 26 faces and is in direct contact with the vitreous humor 30, which is located within the sclera 32 of the eye.

As long as the structure of the capsule 26 that resides in contract with the vitreous humor 30 remains inviolate the nuclear fragments 20 can be aspirated from within the capsule 26 of the lens 28 in the conventional manner as depicted in FIG. 1. However, due to the extreme sharpness of the cutting edge 12 and the rapid vibration of the needle 10, both of which are necessary to emulsify the nucleus of the lens 28, not infrequently the needle 10 will slice through the surface of the capsule 26 facing the vitreous humor 30 and create an opening therein which provides a path of flow between the interior of the lens 28 and the vitreous humor 30. Such a slit or tear is indicated at 34 in FIG. 5.

When a tear or slit 34 is created, vitreous humor will well up into the capsule 26 through slit 34. The nuclear fragments 20 then are engulfed by the vitreous humor that has entered the capsule 26. Also, there is a considerable likelihood that nuclear fragments 20 will pass from within the capsule 26 through the slit 34 therein and enter into the cavity of the sclera 32 occupied by the vitreous humor 30. Unless such nuclear fragments 20 are removed before this can occur, they can create serious complications resulting from surgery.

According to the invention a forceps, such as the forceps 40 depicted in FIG. 2 are provided for use in ophthalmic surgery. The forceps 40 are comprised of a pair of elongated arms 42 and 44 which are joined together at their connected ends by a fulcrum connection 46. The arms 42 and 44 have free ends 48 and 50 that are movable in rotation relative to each other about the fulcrum 46. The forceps 40 also have concave cup-shaped implements 52 and 54 located at the extreme tips of the free ends 48 and 50 of the arms 42 and 44, respectively. The cup-shaped implements 52 and 54 are disposed in mutually facing relationship. The cup-shaped implements 52 and 54 have recessed central regions 56 and 58, depicted in FIG. 4, surrounded respectively by cutting edges 60 and 62.

In the embodiment of FIGS. 2-4 each of the cup-shaped implements 52 and 54 has a hollow hemispherical configuration of a diameter about three and about six millimeters. As illustrated in FIG. 4, the cutting edge 62 at the perimeter of the implement 54 is formed with a blade edge, while the perimeter of the cutting edge 60 is formed with a V-shaped indentation adapted to receive the blade edge of the cutting 62. In this way when the implements 52 and 54 are brought together, the cutting edges 60 and 62 cleanly and sharply sever the contents within the enclosure formed between the implements 52 and 54 from the surrounding material.

As a consequence, once a nuclear fragment 20 within the aqueous humor 30 that has entered the capsule 26 has been located, the implements 52 and 54 can be clamped together by the fingers of the eye surgeon performing the operation by pressing on the portions of the lever arms 42 and 44 relatively near the fulcrum 46. The sharp cutting edges 60 and 62 will cleanly slice through the vitreous humor, thus isolating a spherical globule of a nuclear fragment 20 within a small volume of vitreous humor. The forceps 40 are then drawn away from the eye of the patient while the cup-shaped implements 52 and 54 remain pressed together so as to extract the entrapped nuclear fragment 20 from the patient's eye.

FIG. 5 illustrates an alternative embodiment of the forceps of the invention, indicated generally at 40'. The forceps 40' are identical in most respects to the forceps 40 with the exception that the forceps 40' have non-hemisherical implements, one of which is visible at 54', and each of which has the hollow configuration of one half of a spheroid. That is, each of the perimeters of the implements 54' has a cutting blade formed in an elliptical configuration, and the volume enclosed between the implements 54' is the volume generated by an ellipse rotated 360 degrees about its major axis. The minor axis of the ellipse is preferably between about two and six millimeters in distance across from one side of an implement 54' to the other.

To facilitate insertion of the free ends 48 and 50 of the arms 42 and 44 of either the forceps 40 or the forceps 40', the free ends 48 and 50 are both formed of linear sections 64 and 66. The linear sections 64 and 66 on each of the arms reside at an obtuse angle, indicated generally at A, in FIGS. 2 and 5, relative to each other. The angle A is best illustrated in the side view of FIG. 5 and is preferably between about 135 and 150 degrees. When the free ends 48 and 50 of the arms 42 and 44 are formed in this manner, the implements at the tips of the free ends 48 and 50 can be inserted into the eye of a patient while obscuring the vision of the surgeon to only a mininal extent.

The use of the forceps of the invention is illustrated in FIG. 5. The surgeon first visually locates a nuclear fragment 20 of a lens which has become dislodged in the eye 24 of a patient. The cup-shaped implements 54' are then moved into the eye to positions on opposite sides of a nuclear fragment which may have become engulfed in vitreous humor that has passed through the slit 34 and into the lens capsule 26. The implements 54'(or 52 and 54 of the forceps 40) are then passed together to encapsulate the nuclear fragment 20 therebetween and to isolate that fragment from the interior of the eye 24. The implements 54' or 52 and 54 are then held together with the cutting edges 60 and 62 engaged with each other with a zero clearance therebetween. The nuclear fragment 20 trapped within the hollow cavity defined between the implements 52 and 54 or 54' is thereby withdrawn from the vitreous humor 30 so that it cannot create inflammation or cause increased pressure within the eye.

Undoubtedly, numerous variations and modifications of the inventions will become readily apparent to those familiar with the tools of ophthalmic surgery. Accordingly, the invention should not be construed as limited to the specific embodiments of the forceps illustrated nor to the manner of implementation of the method described, but rather is defined in claims appended hereto.

I claim:

1. Forceps for use in ophthalmic surgery comprising a pair of elongated arms both having mutually attached ends joined together at a single common fulcrum connection and opposite free ends movable in rotation relative to each other, and concave cup-shaped implements located at the extreme tips of said free ends of said arms in mutually facing relationship, wherein said cup-shaped implements have recessed central regions and surrounding cutting edges that extend completely around said central regions and which are movable into mutual contact throughout their entire perimeters, whereupon said implements define an isolated, completely enclosed cavity therebetween.

2. Forceps according to claim 1 wherein said cup-shaped implements are both of hollow, hemispherical configuration.

3. Forceps according to claim 1 wherein said cup-shaped implements are both hollow and both have the mating configuration of one half of an oval body.

4. Forceps according to claim 1 wherein one of said cutting edges is formed with a blade and the other of said cutting edges is formed with an identation adapted to receive said blade.

5. Forceps according tp claim 1 wherein said cup-shaped implements have a minimum dimension across said recessed central regions of between about two and about six millimeters.

6. Forceps according to claim 1 wherein said free ends both include linear extremities adjacent said tips which form an obtuse angle with adjacent linear portions of said arms.

7. Forceps according to claim 6 wherein said obtuse angle is between about 135 and 150 degrees.

8. Forceps for use in removing nuclear fragments of the lens of an eye comprising a pair of elongated arms both having mutually attached ends and opposite free ends, said free ends extending in diverging fashion from each other and being biased apart and terminating in mutually facing cup-shaped implements which are concave at their mutually facing central regions and which have perimeters which completely encircle said central regions and which form cutting edges throughout their encircling perimeters that are capable of being brought into mutual contact throughout, whereupon said central regions define an isolated, completely enclosed cavity therebetween.

9. Forceps according to claim 8 wherein each of said free ends is formed of linear sections which reside at an obtuse angle relative to each other.

10. Forceps according to claim 9 wherein said obtuse angle is between about 135 and about 150 degrees.

11. Forceps according to claim 8 wherein each of said implements has a hollow, hemispherical configuration of a diameter of between about two and about six millimeters.

12. Forceps according to claim 8 wherein each of said implements has the hollow configuration of one half of a spheroid and each of said perimeters of said implements has an elliptical configuration.

13. Forceps according to claim 8 wherein the perimeter of at least one of said implements is formed with a blade edge.

14. Forceps according to claim 13 wherein the perimeter of the other of said implements is formed with an indentation adapted to receive said blade edge.

15. A method of removing nuclear fragments of a lens during eye surgery utilizing forceps which are equipped with a pair of mutually facing cup-shaped implements which have recessed central regions and mating peripheral cutting edges completely surrounding said recessed central regions comprising: visually locating a nuclear fragment of a lens which has become dislodged in an eye of a patient, moving said cup-shaped implements into said eye to positions on opposite sides of said nuclear fragment, and pressing said implements together to bring said mating peripheral cutting edges into mutual contact throughout, thereby forming an isolated, completely enclosed cavity between said cup-shaped implements to thereby completely encapsulate said nuclear fragment within said cavity to isolate it from the interior of said eye, and holding said implements together with said mating periperal cutting edges in mutual contact throughout while withdrawing said implements from said eye, thereby withdrawing said nuclear fragment therefrom as well.

* * * * *